US011432709B2

(12) United States Patent
Yoshinaga et al.

(10) Patent No.: US 11,432,709 B2
(45) Date of Patent: Sep. 6, 2022

(54) ENDOSCOPE SYSTEM

(71) Applicant: OLYMPUS CORPORATION, Tokyo (JP)

(72) Inventors: Takuto Yoshinaga, Hachioji (JP); Chikayoshi Meguro, Hachioji (JP); Tatsuhiko Suzuki, Kunitachi (JP)

(73) Assignee: OLYMPUS CORPORATION, Tokyo (JP)

( * ) Notice: Subject to any disclaimer, the term of this patent is extended or adjusted under 35 U.S.C. 154(b) by 260 days.

(21) Appl. No.: 16/861,338

(22) Filed: Apr. 29, 2020

(65) Prior Publication Data

US 2020/0253460 A1 Aug. 13, 2020

Related U.S. Application Data

(63) Continuation of application No. PCT/JP2018/031839, filed on Aug. 28, 2018.

(30) Foreign Application Priority Data

Oct. 31, 2017 (JP) .............................. JP2017-210230

(51) Int. Cl.
*A61B 1/005* (2006.01)
*A61B 1/00* (2006.01)
*A61B 1/012* (2006.01)

(52) U.S. Cl.
CPC ........ *A61B 1/0052* (2013.01); *A61B 1/00002* (2013.01); *A61B 1/00147* (2013.01); *A61B 1/0125* (2013.01); *A61B 1/0014* (2013.01)

(58) Field of Classification Search
CPC .............. A61B 1/00002; A61B 1/0014; A61B 1/00147; A61B 1/0052; A61B 1/0125;
(Continued)

(56) References Cited

U.S. PATENT DOCUMENTS 5,178,130 A * 1/1993 Kaiya .................. A61B 1/0125
348/E5.025
2004/0015050 A1 * 1/2004 Goto .................... A61B 1/0125
600/104
(Continued)

FOREIGN PATENT DOCUMENTS

CN 105473048 A 4/2016
EP 3 035 836 A1 6/2016
(Continued)

OTHER PUBLICATIONS

International Search Report dated Nov. 27, 2018 issued in PCT/JP2018/031839.

*Primary Examiner* — Aaron B Fairchild
(74) *Attorney, Agent, or Firm* — Scully, Scott, Murphy & Presser, P.C.

(57) ABSTRACT

An endoscope system includes: a first endoscope including an insertion section, an operation section, and a bending operation device; a second endoscope including an insertion section, an operation section, and a bending operation device; and a fixing member configured to connect and fix the operation sections to each other such that the bending operation device of the first endoscope is made to protrude toward the operation section of the second endoscope, the bending operation device of the second endoscope is made to protrude toward the operation section of the first endoscope, and the bending operation device of the second endoscope is spaced apart from the bending operation device of the first endoscope toward an insertion section side.

15 Claims, 4 Drawing Sheets

(58) Field of Classification Search
CPC ............ A61B 1/00066; A61B 1/00128; A61B 2017/347; A61M 2039/1077
See application file for complete search history.

(56) References Cited

U.S. PATENT DOCUMENTS

| | | | | |
|---|---|---|---|---|
| 2005/0272975 | A1* | 12/2005 | McWeeney | A61B 1/0125 600/172 |
| 2006/0069304 | A1* | 3/2006 | Takemoto | A61B 1/0014 600/104 |
| 2011/0099773 | A1* | 5/2011 | Golden | A61B 1/00128 24/457 |
| 2014/0171735 | A1 | 6/2014 | Galperin et al. | |
| 2015/0057537 | A1* | 2/2015 | Dillon | A61B 1/0014 600/113 |
| 2020/0245853 | A1* | 8/2020 | Wang | A61B 1/0125 |

FOREIGN PATENT DOCUMENTS

| | | |
|---|---|---|
| JP | 2007-151595 A | 6/2007 |
| JP | 2009-530051 A | 8/2009 |
| JP | 2011-167460 A | 9/2011 |
| JP | 2012-095719 A | 5/2012 |
| JP | 2016-505310 A | 2/2016 |
| JP | 2016-532504 A | 10/2016 |
| WO | WO 2014/091408 A1 | 6/2014 |
| WO | WO 2015/026557 A1 | 2/2015 |

* cited by examiner ated on Aug. 28, 2018 and claims benefit of
ENDOSCOPE SYSTEM

CROSS REFERENCE TO RELATED APPLICATION

This application is a continuation application of PCT/JP2018/031839 filed on Aug. 28, 2018 and claims benefit of Japanese Application No. 2017-210230 filed in Japan on Oct. 31, 2017, the entire contents of which are incorporated herein by this reference.

BACKGROUND OF THE INVENTION

1. Field of the Invention

The present invention relates to an endoscope system having: a first device which includes an operator in an operation section; and a second device which includes an operator in an operation section.

2. Description of the Related Art

An endoscope has been widely used in a medical field. The endoscope generally includes an elongated insertion section. An observation window and an illumination window are formed on a distal end portion of the insertion section.

The insertion section includes a bendable bending portion which is connected to a distal end portion of the insertion section. An operation section is mounted on a proximal end portion side of the insertion section. A bending operation device for performing a bending operation of the bending portion, functional switches for operating endoscope functions and the like are disposed on the operation section.

The endoscope can perform observation, inspection and the like of organs of a subject by inserting the insertion section into a body cavity of the subject.

Further, when necessary, various therapies or treatments can be performed by inserting an elongated insertion section of an endoscope or a treatment instrument, or the like, which forms a second device into a treatment instrument channel formed in an endoscope which forms a first device.

For example, Japanese Patent Application Laid-Open Publication No. 2009-530051 discloses a medical system such as a medical catheter which has manipulable and/or optical functions and an in-vivo visualization system suitable for observing and/or performing diagnostic and therapeutic modality of the inside of a human body such as a biliary tree.

With respect to the above-mentioned medical system, there has been disclosed a configuration where an operation section of a catheter assembly is positioned at and fixed to an operation section of an endoscope by an endoscope connecting device. With such a configuration, one user can operate both the endoscope and the catheter assembly using both hands.

On the other hand, Japanese Patent Application Laid-Open Publication No. 2012-95719 discloses a mother-baby endoscope system formed of: a mother endoscope which has a treatment instrument insertion channel; and a baby endoscope which can perform treatment of the inside of a bile duct or the inside of a pancreatic duct by selectively inserting the baby endoscope into the bile duct or the pancreatic duct from a duodenal papilla through the treatment instrument insertion channel.

With respect to the above-mentioned mother-baby endoscope system, the mother endoscope is operated by a first user, and the baby endoscope is operated by a second user.

Further, in a medical system disclosed in Japanese Patent Application Laid-Open Publication No. 2009-530051, one user grips an operation section of an endoscope with one hand, and performs an operation of a manipulation mechanism of the endoscope with a finger of the hand which grips the operation section.

The user selectively performs holding of an insertion tube of the endoscope or an operation of a manipulation mechanism of a catheter assembly with the other hand.

Then, in operating the manipulation mechanism of the catheter assembly, the user leaves the other hand which is holding the insertion tube from the insertion tube while gripping the operation section of the endoscope with the one hand, and performs an operation of the manipulation mechanism of the catheter assembly with the other hand.

SUMMARY OF THE INVENTION

An endoscope system according to an aspect of the present invention includes: a first device including an insertion section having an elongated shape which is inserted into a subject, an operation section which includes a distal end side portion connected to a proximal end side portion of the insertion section, and an operator which is disposed on the operation section, protrudes in a direction which intersects with a direction in which the insertion section extends, and is operated by a user; a second device including an insertion section having an elongated shape which is inserted into the subject, an operation section which includes a distal end side portion connected to a proximal end side portion of the insertion section, and an operator which is disposed on the operation section, protrudes in a direction which intersects with the direction in which the insertion section extends, and is operated by the user; and a fixing member configured to connect and fix the operation sections to each other such that the operator of the first device is made to protrude toward the operation section of the second device, the operator of the second device is made to protrude toward the operation section of the first device, and the operator of the second device is spaced apart from the operator of the first device toward an insertion section side in the direction in which the insertion section of the first device extends.

DETAILED DESCRIPTION OF THE PREFERRED EMBODIMENT

Hereinafter, an embodiment of the present invention is described with reference to drawings. The drawings are schematic views. Accordingly, it should be noted that a relationship between a thickness and a width of each member, a ratio between thicknesses of respective members and the like differ from the corresponding relationships of members of an actual endoscope system. Needless to say, portions of the endoscope system are described with different size relationships or different ratios between the drawings.

Figure 1:
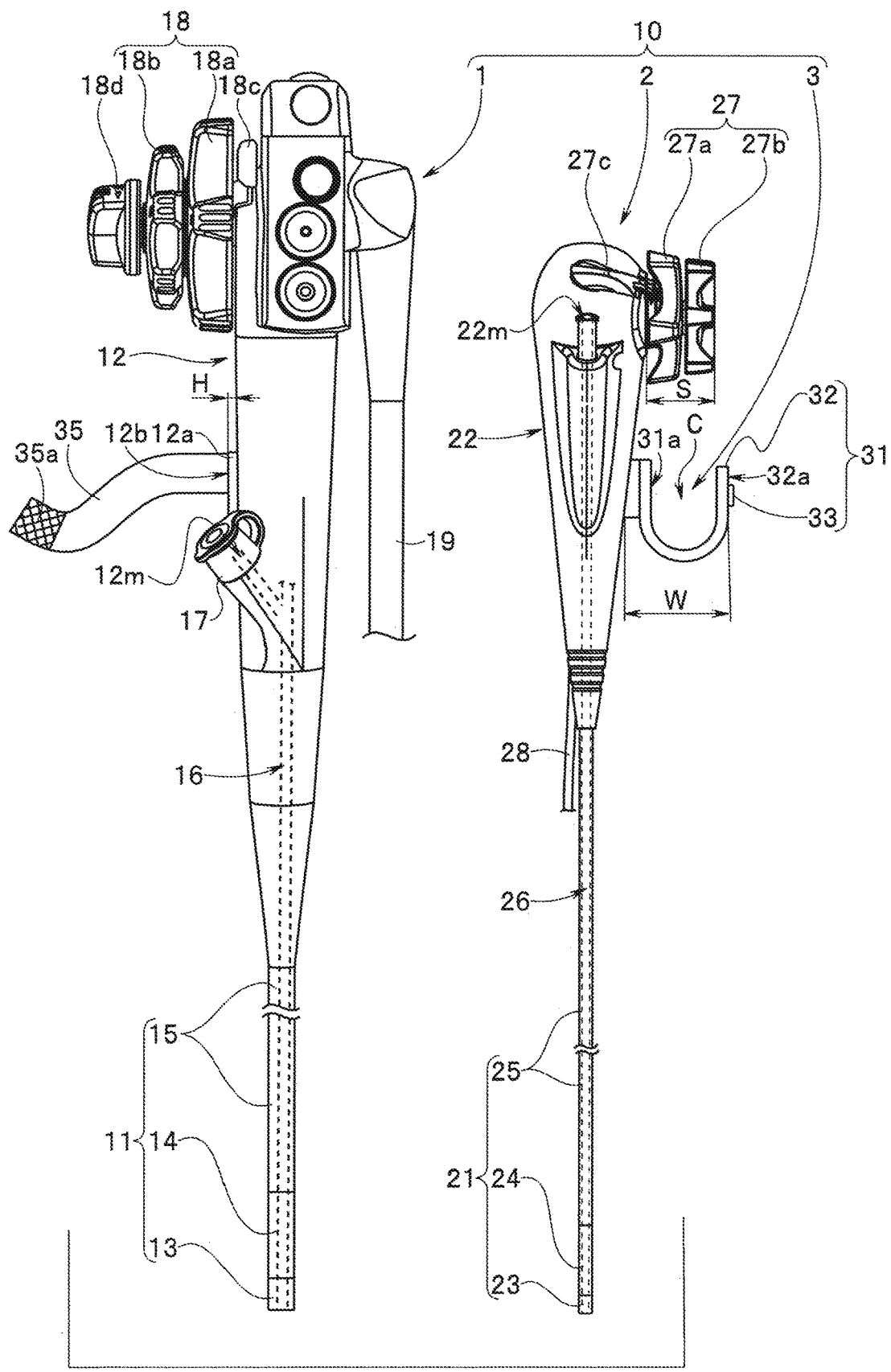
FIG. 1 is a view for describing an endoscope system.

As shown in FIG. 1, an endoscope system 10 according to an embodiment of the present invention has a first endoscope 1 which forms a first device, a second endoscope 2 which forms a second device, and a fixing member 3 which connects and fixes the first endoscope 1 and the second endoscope 2 to each other.

In the above-mentioned configuration, the first endoscope 1 is a so-called mother endoscope, and the second endoscope 2 is a so-called baby endoscope.

The first endoscope 1 is formed of an insertion section 11, and an operation section 12 having a distal end side portion connected to a proximal end side portion of the insertion section 11.

The insertion section 11 is an elongated member and is inserted into a subject. The insertion section 11 is mainly formed by connecting a distal end portion 13, a bending portion 14, and a flexible tube portion 15 in this order from a distal end side.

A treatment instrument insertion channel 16 which is a conduit of the first endoscope 1 is formed in the insertion section 11.

The treatment instrument insertion channel 16 is formed so as to allow a treatment instrument insertion opening 12m formed in the operation section 12 and a distal end opening (not shown in the drawing) of the distal end portion 13 to communicate with each other.

An inner diameter of the treatment instrument insertion channel 16 is set to a size which allows an insertion section 21 of the second endoscope 2 to pass through the treatment instrument insertion channel 16.

Note that a treatment instrument such as a biopsy forceps or a cautery knife which is a second device is also allowed to pass through the treatment instrument insertion channel 16 besides the second endoscope 2. Symbol 17 indicates a forceps plug which is detachably mounted in the treatment instrument insertion opening 12m.

A bending operation device 18 which is an operator is mounted on the operation section 12 in a state where the bending operation device 18 protrudes in a preset direction from a side surface of the operation section.

The bending operation device 18 is operated by a user when the user performs a bending operation of the bending portion 14 of the first endoscope 1.

The bending operation device 18 is a dial, for example. In the present embodiment, the bending operation device 18 includes a vertical bending dial 18a and a lateral bending dial 18b, for example.

The vertical bending dial 18a and the lateral bending dial 18b are respectively mounted on rotary shafts (not shown in the drawing) which protrude in a direction intersecting with a direction in which the insertion section 11 extending from the operation section 12 extends.

The vertical bending dial 18a and the lateral bending dial 18b are rotatably operated about the respective rotary shafts.

Note that symbol 18c indicates a vertical bending braking lever, and symbol 18d indicates a lateral bending braking dial.

Symbol 19 indicates a universal cord which extends from a side portion of the operation section 12. Symbol 12a indicates a holding portion on a first endoscope 1 side, and an engaging portion (symbol 32) which forms a holding portion on a second endoscope 2 side described later is disposed on the holding portion in a preset state.

The second endoscope 2 is formed of the insertion section 21, and an operation section 22 having a distal end side portion which is connected to a proximal end side portion of the insertion section 21.

The insertion section 21 is an elongated member and is inserted into a subject directly or through the treatment instrument insertion channel 16 of the first endoscope 1. The insertion section 21 is mainly formed by connecting a distal end portion 23, a bending portion 24, and a flexible tube portion 25 in this order from a distal end side.

A treatment instrument insertion channel 26 which is a conduit of the second endoscope 2 is formed in the insertion section 21.

The treatment instrument insertion channel 26 is formed so as to allow a treatment instrument insertion opening 22m formed in the operation section 22 and a distal end opening (not shown in the drawing) of the distal end portion 23 to communicate with each other. A treatment instrument such as a laser probe is allowed to pass through the treatment instrument insertion channel 26.

A bending operation device 27 which is an operator is mounted on the operation section 22 in a state where the bending operation device 27 protrudes in a preset direction from a side surface of the operation section.

The bending operation device 27 is operated when a user performs a bending operation of the bending portion 24 of the second endoscope 2. A protruding size of the second bending device 27 of the second endoscope 2 from the second operation section 22 is set to S.

The bending operation device 27 is also a dial. In the present embodiment, the bending operation device 27 includes a vertical bending dial 27a and a lateral bending dial 27b, for example.

The vertical bending dial 27a and the lateral bending dial 27b are respectively mounted on rotary shafts (not shown in the drawing) which protrude in a direction intersecting with a direction in which the insertion section 21 extending from the operation section 22 extends.

The vertical bending dial 27a and the lateral bending dial 27b are rotatably operated about the respective rotary shafts.

Note that symbol 27c indicates a vertical bending braking lever. Symbol 28 indicates a universal cord which extends from a side portion of the operation section 22.

The fixing member 3 is a member which connects and fixes the operation sections to each other in a preset state. In other words, the fixing member 3 integrally connects an area in the vicinity of a distal end side portion of the operation section 22 of the second endoscope 2 (hereinafter, referred to as "second operation section 22") and an area in the vicinity of a distal end side portion of the operation section 12 of the first endoscope 1 (hereinafter, referred to as "first operation section 12"), and defines a distance between the first operation section 12 and the second operation section 22 as a preset distance.

In the present embodiment, the fixing member 3 has holding portions disposed on the first endoscope 1 side and the second endoscope 2 side respectively, and a connecting portion (indicated by symbol 35 described later).

The holding portion on the second endoscope 2 side is a mounting portion 31 having a U shape, for example, which protrudes from a preset position of the second operation section 22 by a preset amount in a direction which intersects with a direction in which the insertion section 21 extends and has a connecting portion arranging gap C.

The mounting portion 31 has an engaging portion indicated by symbol 32 and a positioning portion indicated by symbol 33. Symbol 32a indicates an engaging surface.

Figure 2:
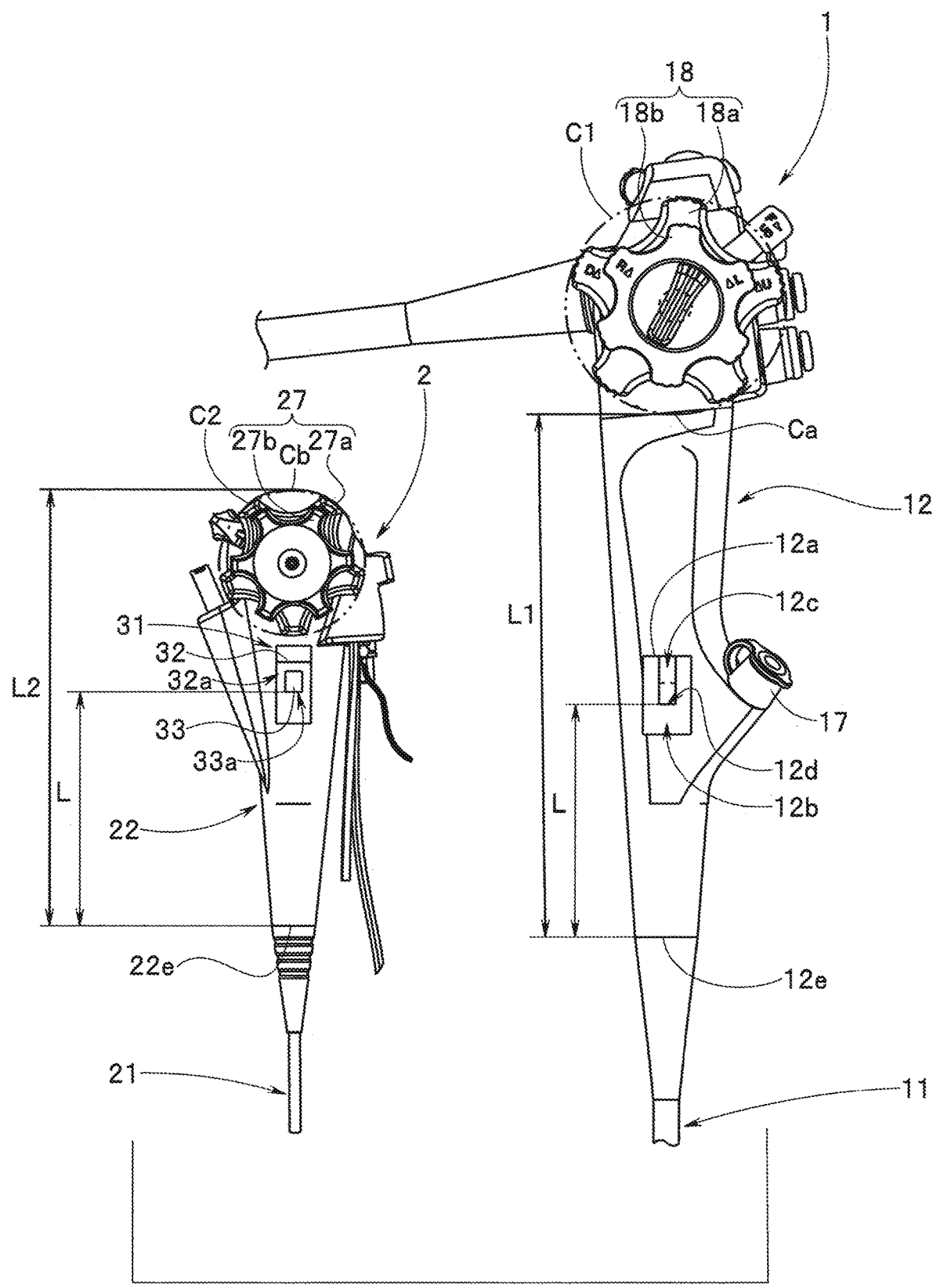
FIG. 2 is a view for describing a relationship between a size of a first device in a direction in which an insertion section of the first device extends and a size of a second device in a direction in which an insertion section of the second device extends.

The positioning portion 33 shown in FIG. 1 and FIG. 2 is a convex portion having a rectangular shape, for example. The positioning portion 33 protrudes by a preset amount W from the engaging surface 32a of the engaging portion 32 which forms the mounting portion 31 (see FIG. 1).

On the other hand, on a defining surface 12b of the defining portion 12a on the first endoscope 1 side, a fitting engaging portion 12c which is a concave portion recessed by a preset amount with respect to the defining surface 12b is formed.

The fitting engaging portion 12c is, for example, a groove formed in the direction in which the insertion section 11 extends. A proximal end side of the fitting engaging portion 12c is opened, and an end part surface 12d is formed on a distal end side of the fitting engaging portion 12c.

A depth of the fitting engaging portion 12c is preliminarily set larger than a protruding amount of the positioning portion 33. As a result, the positioning portion 33 is accommodated in the fitting engaging portion 12c.

Figure 3:
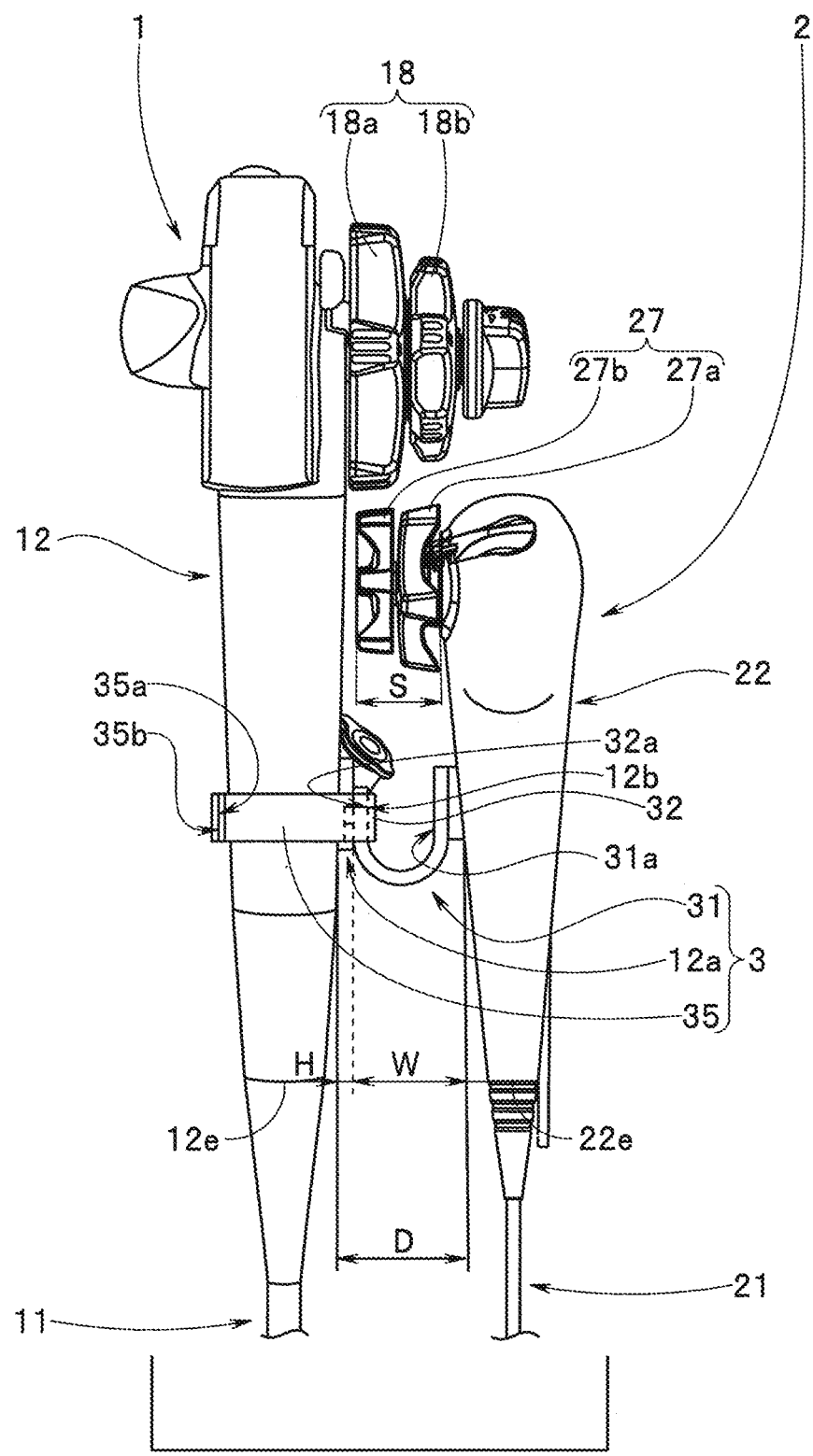
FIG. 3 is a view for describing a state where the operation section of the first device and the operation section of the second device are fixed to each other by a fixing member.

In such an accommodated state, as shown in FIG. 3, the engaging surface 32a of the engaging portion 32 is brought into contact with the defining surface 12b of the defining portion 12a thus bringing about a holding state.

With such a configuration, the first operation section 12 and the second operation section 22 are arranged parallel to the direction in which the insertion section 11 or the insertion section 21 extends.

In this manner, the holding portion is formed of the positioning portion 33 and the fitting engaging portion 12c. The holding portion performs positioning of the second operation section 22 mounted on the first operation section 12 about an insertion axis of the second operation section 22.

Note that the shape of the fitting engaging portion 12c may be formed such that the distal end side is opened and the end part portion is disposed on the proximal end side. The shape of the fitting engaging portion 12c may be formed as a hole which has a shape similar to an outer shape of the positioning portion 33 and into which the positioning portion 33 is fitted.

In the holding state, to allow the second bending device 27 to be arranged in a rotatably operable manner between the first operation section 12 and the second operation section 22, a first size L1 and a second size L2 shown in FIG. 2 are set to satisfy a following relationship, and a distance between the first operation section 12 and the second operation section 22 (see D in FIG. 3) is set to a predetermined size.

As shown in FIG. 2, the first size L1 is a size in the direction in which the insertion section 11 of the first operation section 12 formed on the first endoscope 1 extends.

More specifically, the first size L1 is a distance from a position Ca which is an end position on an insertion section side of an operation trajectory circle C1 of the vertical bending dial 18a in the first bending device 18 formed on the first operation section 12 to a first operation section distal end 12e of the first operation section 12.

On the other hand, the second size L2 is a size in a direction in which the insertion section 21 of the second operation section 22 of the second endoscope 2 extends.

More specifically, the second size L2 is a distance from an end position on a proximal end portion side of the second operation section 22 to a second operation section distal end 22e of the second operation section 22.

The relationship between the first size L1 and the second size L2 is set to L1>L2. Accordingly, the position Ca in the first endoscope 1 and a position Cb which is the end position on a proximal end side of an operation trajectory circle C2 of the vertical bending dial 27a in the second bending device 27 formed on the second operation section 22 are spaced apart from each other.

In the present embodiment, a size from the first operation section distal end 12e of the first operation section 12 to the end part surface 12d and a size from the second operation section distal end 22e of the second operation section 22 to the distal end side surface 33a formed on the mounting portion 31 are set to a size L, for example.

As a result, in a fixed state shown in FIG. 3, the position Ca and the position Cb are spaced apart from each other by (L1-L2) in a state where the position of the first operation section distal end 12e and the position of the second operation section distal end 22e agree with each other.

Note that the second bending device 27 of the second endoscope 2 described above is arranged on a proximal end side of the second operation section 22.

Accordingly, a proximal end side end of the second endoscope 2 is decided based on the arrangement position of the second bending device 27. Accordingly, the proximal end side end of the second endoscope 2 becomes either the proximal end of the second operation section 22 or the position Cb which is the end position on a proximal end side of the operation trajectory circle C2 of the vertical bending dial 27a.

On the other hand, the distance D between the first operation section 12 and the second operation section 22 is set such that the lateral bending dial 27b is not brought into contact with the first operation section 12 in a fixed state shown in FIG. 3.

More specifically, the lateral bending dial 27b is spaced apart from the first operation section 12 by setting the width W of the mounting portion 31 provided with the engaging portion 32 having the engaging surface 32a which is disposed so as to be brought into contact with the defining surface 12b and a protruding height H of the defining portion 12a by taking into account the protruding size S of the second bending device 27.

In other words, in a holding state where the engaging surface 32a of the engaging portion 32 is brought into contact with the defining surface 12b of the defining portion 12a, the protruding size S of the second bending device 27 from the second operation section 22 is set smaller than the distance D between the first operation section 12 and the second operation section 22.

Steps of fixing the first operation section 12 of the first endoscope 1 and the second operation section 22 of the second endoscope 2 to each other, and the manner of operation in a fixed state are described hereinafter.

Figure 4:
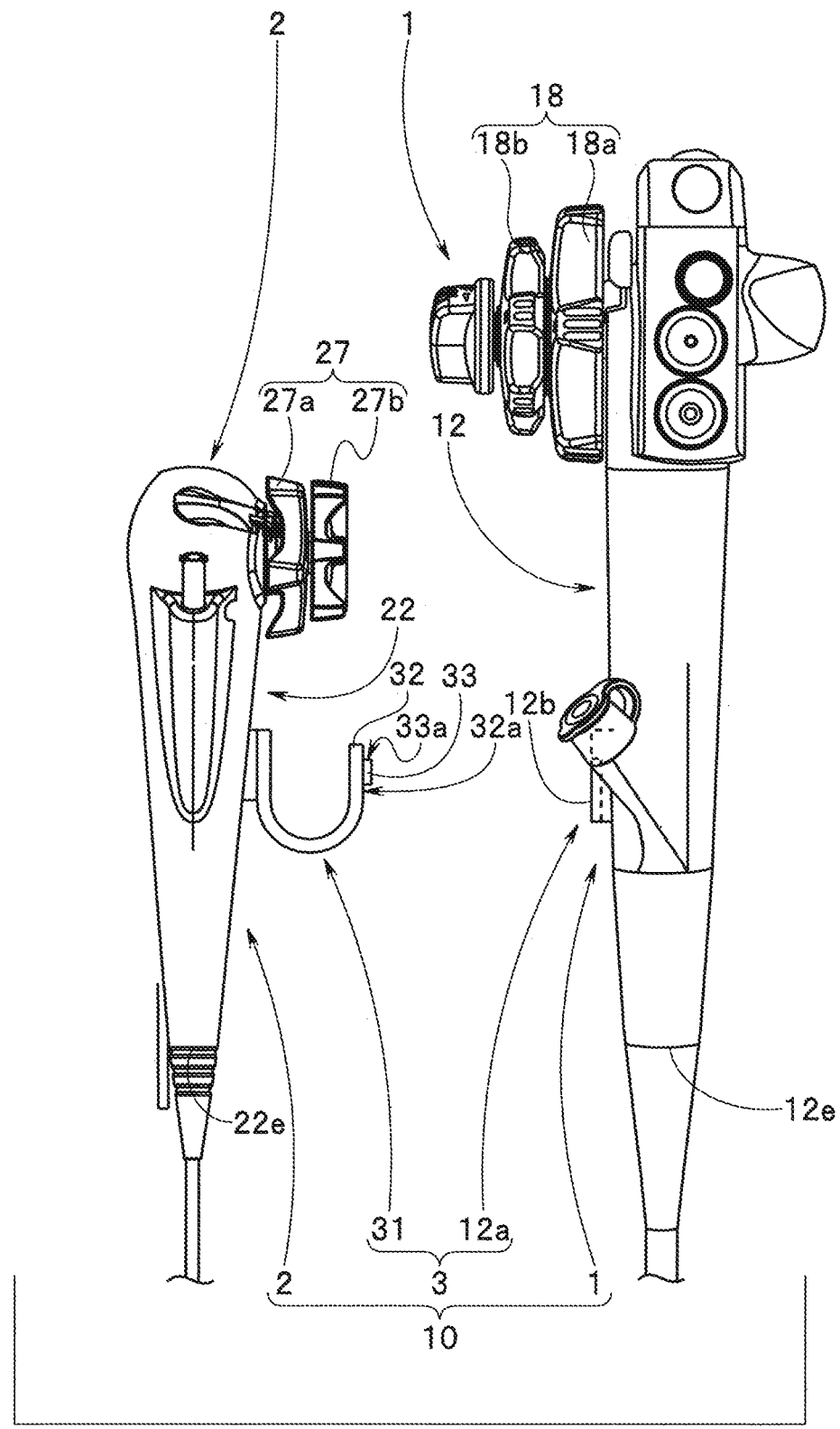
FIG. 4 is a view for describing an arrangement state between the first device and the second device when a user holds the operation section of the first device and the operation section of the second device.

In connecting the first operation section 12 and the second operation section 22 to each other, first, as shown in FIG. 4, the engaging surface 32a of the engaging portion 32 formed on the second operation section 22 and the defining surface 12b of the defining portion 12a of the first operation section 12 are made to opposedly face each other.

In such an opposedly facing state, the bending operation device 18 mounted on the first operation section 12 (hereinafter, referred to as the first bending device 18) protrudes toward the second operation section 22.

On the other hand, the bending operation device 27 mounted on the second operation section 22 (hereinafter, referred to as the second bending device 27) protrudes toward the first operation section 12.

The direction of the treatment instrument insertion opening 12m of the first endoscope 1 and the direction of the treatment instrument insertion opening 22m of the second endoscope 2 are set in substantially the same direction.

Then, as shown in FIG. 3, the engaging surface 32a formed on the second operation section 22 is disposed so as to be brought into contact with the defining surface 12b.

At this stage of operation, as described previously, the positioning portion 33 is accommodated in the fitting engaging portion 12c. Then, the distal end side surface 33a of the positioning portion 33 is brought into contact with the end part surface 12d and hence, the first operation section 12 and the second operation section 22 are brought into a preset holding state.

In such a holding state, the second bending device 27 is disposed in a spaced-apart manner from the first bending device 18 in a direction in which the insertion section 11 extends.

At this stage of the operation, the position Cb which is the end position on a proximal end side of the operation trajectory circle C2 of the vertical bending dial 27a of the second bending device 27 is spaced apart on a more insertion section side than the position Ca which is the end position on an insertion section side of the operation trajectory circle C1 of the vertical bending dial 18a of the first bending device 18 in the direction in which the insertion section 11 of the first endoscope 1 extends, and the second bending device 27 is disposed between the first operation section 12 and the second operation section 22 without being brought into contact with the first operation section 12. As a result, the second bending device 27 is rotatably operable.

In such a holding state, a parallel positional relationship is established between the rotary shaft of the first bending device 18 and the rotary shaft of the second bending device 27.

The first operation section 12 and the second operation section 22 in the above-mentioned holding state are integrally connected and fixed to each other by winding, for example, a strip-shaped face fastener 35 which forms a connecting portion as shown in FIG. 3. In other words, the face fastener 35 is wound around a gap surface 31a of the mounting portion 31 which forms the holding portion mounted on an intermediate portion of the first operation section 12 and an intermediate portion of the second operation section 22.

A width size of the face fastener 35 in the direction in which the insertion section extends is narrower than a width size of the mounting portion 31 which forms the holding portion in the direction in which the insertion section extends. For example, a loop portion 35a which forms the face fastener is mounted on a front surface of the face fastener 35 on one end side, and a hook portion 35b which forms the face fastener is mounted on a back surface of the face fastener 35 on the other end side.

Note that the loop portion 35a may be mounted on the back surface of the face fastener 35 on the other end side and the hook portion 35b may be mounted on the front surface of the face fastener 35 on one end side.

Note that the connecting portion which connects and fixes the first operation section 12 and the second operation section 22 to each other is not limited to a strip-shaped member. The connecting portion may be a clip or the like. In other words, an intermediate portion of the first operation section 12 and an intermediate portion of the second operation section 22 may be connected and fixed to each other by clamping using a clip.

In this manner, as shown in FIG. 3, in a state where the first operation section 12 and the second operation section 22 are fixed to each other, a user can, in a state where the user grips the first operation section 12 of the first endoscope 1 with one hand and grips the insertion section 11 of the first endoscope 1 with the other hand, suitably perform an operation of the vertical bending dial 18a of the first bending device 18, an operation of the lateral bending dial 18b, an operation of the vertical bending dial 27a of the second bending device 27, or an operation of the lateral bending dial 27b with a finger of one hand gripping the first operation section 12.

In other words, without leaving the other hand from the insertion section 11 and keeping gripping of the first operation section 12 of the first endoscope 1 by one hand, the user can, with a finger of one hand, perform an operation of the vertical bending dial 18a of the first endoscope apparatus 18, an operation of the lateral bending dial 18b, the operation of the vertical bending dial 27a of the second bending device 27, or the operation of the lateral bending dial 18b as desired.

The direction of the treatment instrument insertion opening 12m of the first endoscope 1 and the direction of the treatment instrument insertion opening 22m of the second endoscope 2 are directed substantially in the same direction. Accordingly, the user can easily and selectively introduce the treatment instrument into a body of a subject through the treatment instrument insertion channel 16 of the first endoscope 1 or the treatment instrument insertion channel 26 of the second endoscope 2.

Note that the vertical bending dial 18a and the vertical bending dial 27a may be configured such that when both vertical bending dials 18a, 27a are rotated in the same direction, the bending portions 14, 24 are bent in the same direction, or may be configured such that the bending portions 14, 24 are bent in the same direction by rotating one dial toward the other dial. The same goes for the lateral bending dial 18b and the lateral bending dial 27b.

In the above-mentioned embodiment, a parallel positional relationship is established between the rotary shaft of the first bending device 18 and the rotary shaft of the second bending device 27.

However, by taking into account the operability of the first bending device 18 and the operability of the second bending device 27, the defining surface 12b may be formed in an inclined surface with respect to the engaging surface 32a, and the rotary shaft of the second bending device 27 may be suitably inclined with respect to the rotary shaft of the first bending device 18.

In the above-mentioned embodiment, a proximal end side of the fitting engaging portion 12c formed on the first endoscope 1 is opened, and the end part surface 12d is disposed on a distal end side of the fitting engaging portion 12c.

Usually, in many cases, the proximal end side of the operation section is positioned above the distal end side in the direction of gravity when the endoscope is used. Accordingly, when the operation section 12 of the first endoscope 1 and the operation section 22 of the second endoscope 2 are used in a connected state, the end part surface 12d of the first endoscope 1 supports the positioning portion 33 of the second endoscope 2 and hence, the more reliable connection can be realized between the first endoscope 1 and the second endoscope 2.

The present invention is not limited only to the above-mentioned embodiment, and various modifications are conceivable without departing from the gist of the present invention.

What is claimed is:

1. An endoscope system comprising:
    a first device and a second device each comprising:
        an insertion section having an elongated shape configured to be inserted into a subject,
        an operation section disposed on a proximal end side of the insertion section, and
        an operator protruding from a surface of the operation section along an axis which intersects with a longitudinal axis of the insertion section; and
    a fixing member configured to connect and fix the first device and the second device to each other, wherein:
        the fixing member comprising a first fitting portion that protrudes from an outer surface of the operation section of the second device, the first fitting portion having a U shape protruding from the outer surface of the operation section of the second device, one end of the U shape is attached to the second device and an other end of the U shape has a convex portion protruding away from the second device;
        the fixing member further comprising a second fitting portion, the second fitting portion comprising a concave portion disposed on the first device, the convex portion being configured to fit in the concave portion to fix the second device to the first device;
        the fixing member is configured to separate the first and second devices from each other by an amount greater than or equal to a protrusion amount of the operator of the second device; and
        the fixing member is configured to fix the first device and the second device together so that, when the first device is connected and fixed to the second device, the operator of the first device protrudes toward the operation section of the second device, the operator of the second device protrudes toward the operation section of the first device and the operator of the second device is separated from the operator of the first device longitudinally toward the insertion section of the first device.

2. The endoscope system according to claim 1, wherein the first device is a first endoscope and the second device is a second endoscope.

3. The endoscope system according to claim 2, wherein a distance between the operation section of the first device and the operation section of the second device in directions in which the operators protrude is set larger than a protruding size of the operator of the second endo scope.

4. The endoscope system according to claim 1, wherein the operator of the second device is disposed on a proximal end side of the operation section of the second device.

5. The endoscope system according to claim 1, wherein the operator of the first device and the operator of the second device are dials which are rotated about respective rotary shafts extending in protruding directions of the operators.

6. The endoscope system according to claim 5, wherein the rotary shaft of the operator of the first device and the rotary shaft of the operator of the second device are disposed parallel to each other.

7. The endoscope system according to claim 1, wherein the fixing member is disposed at a position between a distal end of the operation section of the first device and the operator of the first device and a position between a distal end portion of the operation section of the second device between a distal end side portion of the operation section and the operator of the second device.

8. The endoscope system according to claim 1, wherein a size of the operation section of the second device in a longitudinal axis direction is smaller than a size of the operation section of the first device from a distal-most trajectory of the operator of the first device to a distal end of the operation section of the first device.

9. The endoscope system according to claim 1, wherein the fixing member includes, at a portion where the operation section of the first device and the operation section of the second device engage with each other, a holding portion for positioning the operation section of the first device and the operation section of the second device about an insertion axis.

10. The endoscope system according to claim 1, wherein the operation section of the first device and the operation section of the second device are connected and fixed to each other by the fixing member such that the operation section of the first device and the operation section of the second device are disposed parallel to each other in the direction in which the insertion sections extend.

11. The endoscope system according to claim 1, wherein a connecting portion connects the one end of the U shape to the other end of the U shape, and
    a size of the connecting portion in the direction in which the insertion sections extend is set smaller than a size of the one end and the other end in the direction in which the insertion sections extend.

12. The endoscope system according to claim 1, wherein the operator of the first device is configured to perform a bending operation of a bending portion formed on a distal end side of the insertion section of the first device, and
    the operator of the second device is configured to perform a bending operation of a bending portion formed on a distal end side of the insertion section of the second device.

13. The endoscope system according to claim 12, wherein the operator of the first device and the operator of the second device are set such that the bending portion of the first device and the bending portion of the second device are bent in a same direction when the operator of the first device and the operator of the second device are rotated in a same direction or when the operator of the first device and the operator of the second device are operated toward the operator of the second device and the operator of the first device respectively.

14. The endoscope system according to claim 1, wherein the first device includes a conduit which allows an area in a vicinity of the operation section of the first device and a distal end of the insertion section of the first device to communicate with each other, and an inner diameter of the conduit is set to a size which allows the insertion section of the second device to pass through the conduit.

15. The endoscope system according to claim 14, wherein the second device including the insertion section which is allowed to pass through the conduit of the first device further includes a conduit which allows the area in the vicinity of the operation section of the second device and the distal end of the insertion section of the second device to communicate with each other, and
    a direction of an inlet of the conduit which the second device includes and a direction of an inlet of the conduit which the first device includes are a same direction in a state where the operation section of the first device and the operation section of the second device are connected and fixed to each other by the fixing member.

\* \* \* \* \*